Figure 1:
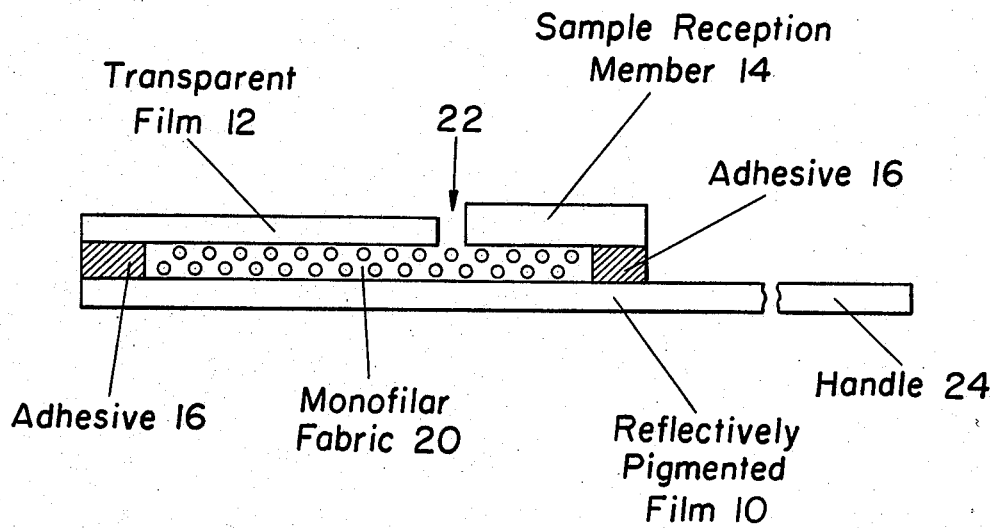

United States Patent [19]

Vogel et al.

[11] Patent Number: 4,582,684
[45] Date of Patent: Apr. 15, 1986

[54] CUVETTE FOR THE PHOTO DETERMINATION OF CHEMICAL COMPONENTS IN FLUIDS

[75] Inventors: Peter Vogel, Hemsbach; Walter Rittersdorf, Mannheim, both of Fed. Rep. of Germany

[73] Assignee: Boehringer Mannheim GmbH, Mannheim, Fed. Rep. of Germany

[21] Appl. No.: 531,439

[22] Filed: Sep. 12, 1983

[30] Foreign Application Priority Data

Sep. 11, 1982 [DE] Fed. Rep. of Germany ....... 3233809

[51] Int. Cl.[4] ...................... G01N 21/03; G01N 33/52
[52] U.S. Cl. ...................... 422/57; 356/246; 422/58
[58] Field of Search ............ 422/102, 58, 56, 57, 422/61; 356/246

[56] References Cited

U.S. PATENT DOCUMENTS

| 29,725 | 8/1858 | Johnson et al. | 422/61 |
|---|---|---|---|
| 3,420,205 | 1/1969 | Morison | 422/56 X |
| 3,510,263 | 5/1970 | Hach | 422/56 X |
| 3,690,836 | 9/1972 | Buissiere et al. | 422/56 |
| 3,715,192 | 2/1973 | Wenz et al. | 422/56 |
| 3,791,933 | 2/1974 | Moyer et al. | 422/56 X |
| 3,811,840 | 5/1974 | Bauer et al. | 422/56 |
| 3,917,453 | 11/1975 | Milligan et al. | 422/56 X |

FOREIGN PATENT DOCUMENTS

| 0054679 | 6/1982 | European Pat. Off. |
| 2215089 | 10/1973 | Fed. Rep. of Germany |
| 2325920 | 4/1977 | France |

*Primary Examiner*—Arnold Turk
*Attorney, Agent, or Firm*—Felfe & Lynch

[57] ABSTRACT

A cuvette for the determination of a chemical component of a fluid by photo evaluation has two planar-shaped parts parallel to one another at least one of which is transparent in the spectral range used for the evaluation. A planar distance piece of a filamentary reticulation for receiving the fluid therein spaces the planar-shaped parts apart to set the length of the light path through the cuvette for the photo evaluation.

20 Claims, 2 Drawing Figures

CUVETTE FOR THE PHOTO DETERMINATION OF CHEMICAL COMPONENTS IN FLUIDS

The present invention relates to a cuvette for the photo determination of a chemical component in a fluid and, more particularly, determination by spectrophometric evaluation.

Spectrophometric analysis is one of the methods of investigation of fluids which is most frequently used in industry, purity testing, quality control, reaction regulation and control, and qualitative and quantitative analyses being conventional fields of use. In clinical chemistry, for the recognition of diseases of the human body, its use is also conventional to determine the concentration of particular compounds in the blood, serum and urine.

Processes suitable for these purposes have long been known. They generally test for the substance to be determined with transmission photometers, usually after dilution of the sample material. For these processes, which are usually only to be used stationary, there are conventionally employed glass or synthetic resin cuvettes with a standard path-length of 1 cm. In exceptional cases, cuvettes with other path-lengths are also used.

From the Lambert-Beer Law ($A = \epsilon \cdot c \cdot d$) used for transmission photometry, it can be readily deducted that, for measuring absorbances in the range of $A = 0.1$ to 1 in conventional sample concentrations of $c = 10^{-5}$ to $10^{-4}$ mol/liter having a molar extinction coefficient of $\epsilon = 10^4 \, \text{Mol}^{-1} \cdot \text{l} \cdot \text{cm}^{-1}$, a path-length d of about 1 cm. is needed, corresponding to the standard cuvette path-length. Problems then arise when the substances to be determined occur in comparatively high concentrations. In this case, the sample is usually diluted.

For the avoidance of pipetting and dilution errors, there has long been a tendency in analytical chemistry to use undiluted sample material for analytical purposes. Furthermore, attempts have been made to keep the required sample volume as small as possible, since frequently only small amounts are available but also, for reasons of cost, to limit the amount of reagents required. One of the solutions of this problem are test strips, which have been known for many years, which contain the chemicals required for the reaction and which are used for analytical purposes by dipping into or spotting with small sample volumes of the fluid to be investigated, the concentration of the substance to be determined being determined by comparison with a colour scale or by remission photometrical measurement of the reaction colours. However, because of the inhomogeneity of the carrier materials (papers), the test strips frequently do not provide the necessary precision or, for example, in the case of water-stable transparent films (see, for example, Federal Republic of Germany Patent Specification No. 15 98 153), the necessary colour intensity cannot be achieved in all cases. An additional problem of these rapid tests based upon absorbent carriers or films is the fact that the substrate dosaging must take place very precisely or that, in the case of inexact dosaging, an excess must be removed. A further conceivable solution to the problem in the case of small volumes is offered by a reduction of the path-length of the cuvette, which is certainly technically possible with rigid materials, for example glass or thermosetting resins (such as are described in Federal Republic of Germany Patent Specification No. 27 29 294) but can only be achieved laboriously and with high costs. Disposable articles which are cost-favourable to produce are, on the other hand, difficult to make with the necessary tolerance of the cuvette thickness of 5%.

From U.S. Pat. No. Re. 29,725, it is known to mix reagents and sample in an analysis container which consists of two flexible films connected together on the edge and to bring them to reaction and, inter alia, to measure the reaction product spectrophotometrically. For this purpose, the analysis container is laid between two plane-parallel "jaws" arranged at a definite distance from one another in the light path of the spectrometer and, by pressure on the outer region of the analysis container, the inner pressure is increased until the transparent walls lie smoothly against the "jaws". The distance between the "jaws" minus twice the thickness of the films then defines the path-length of the "cuvette". Here, again, it is difficult to produce the films with a tolerance of less than 5% in the thickness thereof. Since this error enters twice into the path-length of the cuvette, path-lengths of less than 1 mm. can only be achieved inexactly.

One of the prime objects of the present invention is to provide a cuvette which permits the determination of chemical components in fluids and which combines the advantages of the presence of the reagents on test strips with the analytical precision in the case of the use of definite cuvette path-lengths with, at the same time, small sample volumes.

Thus, according to the present invention, there is provided a cuvette for the determination of a chemical component of a fluid by photometric evaluation through the fluid in the cuvette. The cuvette comprises two, non-absorbent, planar-shaped parts, either both parts being transparent in the spectral range used for the evaluation or one part being so transparent and one part preferably providing high reflectance in the spectral range. Between these planar shaped parts is a similarly-transparent, substantially-planar distance piece which is a filamentary reticulation for receiving the fluid and spacing the planar-shaped parts in parallel to one another, the length of the light path through the cuvette for the evaluation thus being predetermined by the thickness of the distance piece across a sufficient number of the filaments, for example between 20 and 500 per cm. The planar shaped parts (preferably films) and, preferably, the distance piece are joined together at least at one edge thereof and separate at least at one edge thereof, i.e., being joined at fewer than all the edges thereof.

When using the cuvette according to the present invention, the sample is introduced into the cuvette chamber via a lateral opening with the capillary action of the distance piece. We have also found that the reagents necessary for a chemical reaction can be applied either to the surface of one or both films which bound the cuvette or on the distance piece or can be fixed in a sample reception and reaction zone provided before the cuvette opening, the sample material thereby being passed through the reaction zone before entering the cuvette.

Surprisingly, we have now found that, in the case of the use of monofilar fabrics for the distance piece, such as are produced, for example, in large amounts for use as sieve material, with sample volumes of only a few μl., variation coefficients of 1% can be maintained in repeated spectrophotometric measurements although the thicknesses of the individual filaments differ by 5%, when the sufficient number of filaments per cm is kept constant. Although, due to the capillary action of the distance piece, the shaped parts of the cuvette in the filled state are already relatively close together, it is advantageous, during the measurement, to exert a light external pressure on the shaped parts and thus to guarantee a close proximation to the distance piece and thus a constant path-length of the cuvette. The shaped parts are advantageously also made from synthetic resin films.

This surprising constancy of the measurements can be explained in that, for the measurement, the total space between the shaped parts is not relevant but only the space remaining between the shaped parts and the filaments of the distance piece, which defines an apparent path-length of the cuvette. This apparent path-length is less influenced by material tolerances since, on the one hand, a range over several filaments is used for the measurement so that errors are already compensated and, on the other hand, for example, an enlargement of the shaped part distance due to thicker filaments simultaneously brings about a reduction of the hollow spaces in the distance piece because the filaments lie closer together so that these changes are substantially mutually compensated.

These synthetic resin cuvettes can be produced very simply in comparatively large numbers by sticking together the materials in band form on one or both longitudinal edges and subsequently cutting up transversely thereto to give strips of suitable width.

The reticulation forming the distance piece consists of non-absorbent material which is insoluble in the sample, is transparent and only has a low adsorption. The reticulation can be woven or knitted from individual filaments (monofilar) or from twisted filaments which consists of several thin individual filaments (multifilar). The reticulation is advantageously built up in the form of a monofilar fabric. Multifilar reticulations are less suitable since the filament shape can change more under pressure.

The material of the reticulation can thereby consist of water-insoluble polymers or polycondensates, for example of polyesters, polyamides, polycarbonates, polystyrene, polyurethanes and the like. Because of their inertness, glass fibres would be especially suitable but fabrics with suitable thicknesses and tolerances are not commercially available. The filaments from which the fabric is made can have a thickness of from about 10 to 200$\mu$. In the case of monofilar fabrics, the preferred thickness is from 20 to 100$\mu$.

The thickness of the reticulation depends upon the filament thickness and upon the nature of the fabric and can be from 30 to 500$\mu$ but is preferably from 40 to 200$\mu$. In the case of normal fabrics, it corresponds to the thickness of the cross-over points, e.g. the thickness of two filaments.

The transparent planar shaped parts are of a material which is non-absorbent and insoluble in the fluid or sample to be evaluated. They can be made of glass but also of a synthetic resin film which, for example, can be the same as the material of the reticulation. The thickness of the material used is not critical since it does not form part of the path-length of the cuvette, in contradistinction to the device according to U.S. Pat. No. Re. 29,725. However, for practical reasons it is from 0.05 to about 1 mm.

The light-reflecting boundary of the cuvette can consist of metal, glass, ceramic, synthetic resin or other reflecting material and the light reflectance can be produced by providing a reflecting coating or a surface gloss or by pigmenting the material. The side facing the cuvette should be planar, impermeable and non-absorbing. The path-length of the cuvette chamber is given by the thickness of the reticulation. As stated above, this is preferably achieved by pressing together the shaped parts by the optics of the spectrophotometer with a pressure of 0.1 to 10 bar so that, during the measurement procedure, the cuvette path-length assumes a constant and reproducible value given by the material properties of the reticulation. If the shaped parts are firmly connected together, at least one of the bounding materials must be of a flexible material or the material connecting point must be elastically formed. The cuvette is advantageously open on at least one side so that any excess of sample present can escape upon pressing together. The cuvette can be kept in shape by adhesion, welding or clamping of all three constructional parts of the cuvette but at least of the shaped parts bounding the cuvette. This can take place on one side, on opposite-lying sides or on all sides as long as less than all the perimeter is joined. Filling with the sample material to be measured can thereby also take place from one or more sides as well as from the front or the back (i.e., top or bottom) through appropriate openings.

In order to facilitate the flowing in of the sample material, the surfaces of the distance piece and of the shaped parts should be hydrophilic or be appropriately finished. Furthermore, the surfaces can be covered with one or more reagents, which can be achieved by preliminary treatment, for example by dipping, spraying or coating with wetting agents or reagent solutions.

In many cases, it is appropriate, before carrying out the measurement or before the completion of the reaction taking place in the cuvette, to separate certain components from the sample or to allow a preliminary reaction to take place under other conditions. For this purpose, outside the actual cuvette chamber provided for the measurement, there can be provided a separate separation and/or reaction zone to which the sample is applied and from which it is transferred to the cuvette after completion of the separation or preliminary reaction step. In the simplest case, this transfer can be brought about by a capillary contact with the distance piece. In special cases, for example when a chronologically defined preliminary reaction is to take place, the transfer can also take place actively, for example by pressing together of the reaction zone.

For attaching a sample reception zone, at least one of the shaped parts is extended by an appropriate amount beyond the length of the cuvette part defined by the distance piece. An additional elongation can be advantageous as a handle and to provide a space for marking or identification.

The separation or reaction zone should consist of an absorbent material, for example a paper or a fleece of a synthetic resin or of a synthetic resin-cellulose mixture or other similar material, which is provided with the necessary reagents by spraying or impregnation. Insofar as these reagents disturb the following measurement, they can be carrier-fixed.

Ion-exchange papers can be used for the separation of disturbing ions and appropriate filter materials for the separation of corpuscular material. An excess of sample which is not to be taken up by the cuvette can also be removed in this zone to permit an unmeasured application of the sample.

The cuvette according to the present invention can be so modified that it comprises all transparent materials.

So that the determination can take place by transillumination, a light source being positioned on one side of the cuvette and a light-sensitive detector being positioned on the other side thereof. However, the determination can also take place by reflectance photometry, a light source and a photodetector being arranged on the same side of the cuvette. The cuvette according to the present invention can also be used completely without chemical reagents when the sample to be analysed consists of a coloured fluid for example a dyebath or an ink, or when, for example, the concentration of erythrocytes in blood or the content of bilirubin in serum is to be measured.

Since, in contradistinction to the previously known cuvettes, the path-length of which is determined by means lying outside of light path (side walls of the standard cuvettes and the "jaws" according to U.S. Pat. No. Re. 29,725), the distance piece lies in the light path, apart from special cases in which the filaments and sample possess the same refractive index, additional refractions on the filament surfaces are to be taken into account. Therefore, in order to avoid scattering losses, the detector side of the spectrometer must be so constructed that the scattered light is also picked up. For this, a focusing lens must be provided directly behind the cuvette, or an Ulbricht sphere-type photometer used. Otherwise, conventional spectrometer arrangements can be used.

Figure 2:
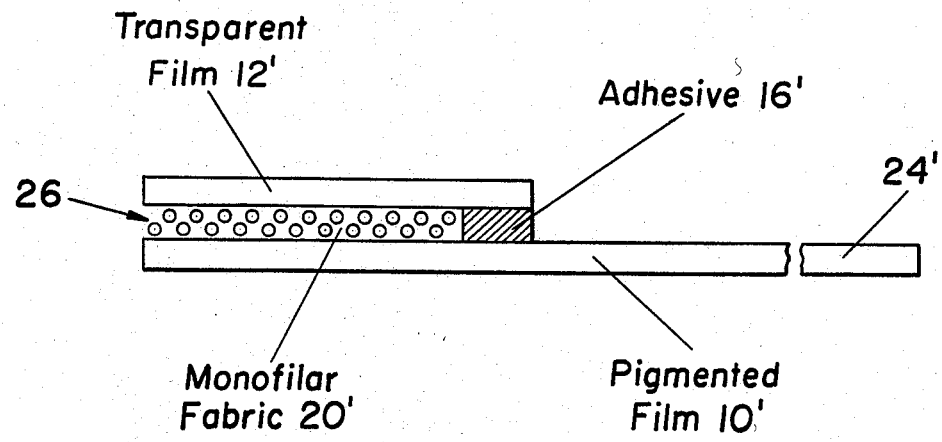

Illustrative preferred embodiments of the present invention are shown in the accompanying drawings, wherein:

FIG. 1 shows a cuvette with a sample reception zone in cross-sectional elevation; and FIG. 2 shows a cuvette without a sample reception zone in cross-sectional elevation.

FIG. 1 shows a reflectively-pigmented film 10, a transparent film 12, and a sample-reception member (e.g. a reagent-impregnated fleece) 14 which are stuck together as two spaced layers with a melt adhesive 16 at least along the two opposite edges shown. A monofilar fabric 20 may be adhered to the pigmented film with an adhesive (not shown) or merely pinched between the layers. The sample-reception member 14 is in capillary communication with the fabric 20. Any excess sample can escape from the fabric at the gap at 22 upon pressing the layers together. The pigmented film 10 is extended at one end to form a handle 24.

FIG. 2 shows a similar reflectively-pigmented film 10' and a transparent film 12' which are stuck together on one edge with a melt adhesive 16'. The monofilar fabric 20' is similarly stuck to the pigmented film or pinched between the layers. The sample is introduced into the cuvette chamber via a lateral opening at 26 with capillary action of the monofilar fabric 20'.

The following Examples are given for the purpose of illustrating the present invention:

EXAMPLE 1

Agent for the determination of haemoglobin in blood
0.3 g. dioctyl sodium sulphosuccinate
0.3 g. diamyl sodium sulphosuccinate
2.5 g. saponin
2.0 g. potassium ferricyanide
9.0 g. mercuric cyanide are dissolved in 100 ml. 0.1 mol citrate buffer. With this solution there is impregnated a 500µ thick polyamide fleece (SL 4207 KA of the firm Kalff) and subsequently dried at 60° C. The impregnated fleece is cut up into strips of 6 mm. width.

From strips of (a) a polystyrene film, pigmented with titanium dioxide, of 500µ thickness and 77 mm. width, (b) a transparent polycarbonate film (Pokalon N, transparent of the firm Lonza AG) of 150µ thickness and 15 mm. width, (c) monofilar polyamide fabric (NY 15 HC of the firm Züricher Beuteltuchfabrik) with a filament thickness of 30µ and a filament number of 222, which has been washed with 0.05% dioctyl sodium sulphosuccinate in water, with a width of 15 mm. and (d) the impregnated fleece there is assembled and stuck together, with a melt adhesive applied from a heated nozzle, an arrangement as illustrated in FIG. 1 of the accompanying drawings. The band-like arrangement is subsequently cut up into 6 mm. wide strips. On to the 6×6 mm. sized sample reception zone (fleece) of such a cuvette there are dropped about 25 µl. of blood. The blood now flows over the reaction fleece, in which the erythrocytes are haemolysed and the haemoglobin thereby liberated is reacted to give haemoglobin cyanide into the cuvette slot. The reaction colour of the haemoglobin cyanide is measured on reflectance photometer PMQ III with sphere attachment KA of Zeiss at 540 nm., the test strip being applied with the side with the transparent film in front of the measurement opening and is pressed on with a planeground magnet (0.5 bar). By means of a calibration curve previously determined with haemoglobin solutions, the reflectance values can be converted into haemoglobin concentrations. With this arrangement, in the concentration range of 25 to 200 g. haemoglobin/liter, there can be carried out haemoglobin determinations from blood with a precision from day to day of 2% (variation coefficient).

TABLE I

| haemoglobin concentration g./liter | reflectance % |
|---|---|
| 19 | 55 |
| 57 | 35.1 |
| 85 | 28.5 |
| 123 | 23.4 |
| 140 | 21.2 |
| 174 | 17.9 |
| 209 | 15.8 |
| 233 | 14.3 |

EXAMPLE 2

Agent for the determination of bilirubin in serum

From strips of (a) a pigmented polystyrene film of 500µ thickness and 77 mm. width, (b) a transparent polyacetate film (Ultraphan of the firm Lonza) of 200µ thickness and 15 mm. width, (c) a monofilar polyester fabric (PE 73 HC of the firm Züricher Beuteltuchfabrik) with a filament thickness of 38µ, a filament number of 89.5 and 15 mm. width and (d) a glass fibre fleece of 60 g./m² (No. 9 of the firm Schleicher & Schüll), which has been impregnated with a solution of 5% potassium ferricyanide in water, with a width of 6 mm., there is assembled and stuck together an arrangement according to Example 1 (FIG. 1) which is then cut up into 6 mm. wide strips. 20 µl. of bilirubin-containing whole blood are dropped on to the sample reception fleece. The glass fibre fleece retains the blood corpuscles. The serum with the bilirubin oxidised to biliverdin flows into the cuvette slot and is measured as in Example 1 on reflectance photometer PMQ 3 at 630 nm. The bilirubin concentration in the serum can thus be determined via a calibration curve.

EXAMPLE 3

Agent for the determination of the concentration of Evan's blue in aqueous solutions From strips of (a) a pigmented polystyrene film of 500μ thickness and 77 mm. width, (b) a transparent polyester film of 100μ thickness and 15 mm. width and (c) a monofilar polyamide fabric (NY 64 HC of the firm Züricher Beuteltuchfabrik) of 15 mm. width, there is assembled and stuck together an arrangement according to FIG. 2 which is then cut up into strips of 10 mm. width. The lower edges of the strips are carefully brought into contact with the surface of an aqueous solution of Evan's blue, the cuvette chamber thereby filling immediately with the solution. The filled strips are measured on reflectance photometer PMQ III at 640 nm with spheroidal attachment KA of Zeiss and the remission values obtained can be converted via a calibration curve into concentrations. In the case of repeated measurements (n=10), in the concentration range of 0.01 to 1.0 mmol/liter, there is measured a variation coefficient of about 1% in the case of a bias of 2%.

TABLE II

| concentration mmol/l. | reflectance % |
| --- | --- |
| 0.000 | 78 |
| 0.100 | 66 |
| 0.250 | 54 |
| 0.500 | 43 |
| 0.750 | 33 |
| 1.000 | 26.5 |

It will be understood that the specification and examples are illustrative but not limitative of the present invention and that other embodiments within the spirit and scope of the invention will suggest themselves to those skilled in the art.

What is claimed is:

1. A cuvette for the determination of a chemical component of a fluid by photometric evaluation through the fluid, comprising:
   two, non-adsorbent, planar-shaped parts at least one of which is transparent in the spectral range used for the evaluation, the planar-shaped parts being joined together at less than all their perimeters; and
   a similarly-transparent, substantially-planar distance piece comprising a filamentary reticulation between the two planar-shaped parts for receiving the fluid and spacing the planar-shaped parts in parallel to one another by the thickness of the distance piece across a sufficient number of filaments to thereby determine a definite path length of light through the cuvette for the evaluation.

2. The cuvette of claim 1, wherein the distance piece is one of a monofilar and multifilar fabric of from about 30μ to about 500μ thick of synthetic resin filaments of from about 10μ to about 200μ thick.

3. The cuvette of claim 1, and additionally comprising a reagent for reaction with the fluid for the evaluation on a surface of at least one of the two planar-shaped parts facing a surface of the other.

4. The cuvette of claim 2, and additionally comprising a reagent for reaction with the fluid for the evaluation on a surface of at least one of the two planar-shaped parts facing a surface of the other.

5. The cuvette of claim 1, and additionally comprising an absorbent fluid-reception member in fluid communication with the distance piece.

6. The cuvette of claim 2, and additionally comprising an absorbent fluid-reception member in fluid communication with the distance piece.

7. The cuvette of claim 3, and additionally comprising an absorbent fluid-reception member in fluid communication with the distance piece.

8. The cuvette of claim 4, and additionally comprising an absorbent fluid-reception member in fluid communication with the distance piece.

9. The cuvette of claim 5, wherein the absorbent fluid-reception member comprises means operative on the fluid for at least one of reaction therewith and separation of components thereof.

10. The cuvette of claim 6, wherein the absorbent fluid-reception member comprises means operative on the fluid for at least one of reaction therewith and separation of components thereof.

11. The cuvette of claim 7, wherein the absorbent fluid-reception member comprises means operative on the fluid for at least one of reaction therewith and separation of components thereof.

12. The cuvette of claim 8, wherein the absorbent fluid-reception member comprises means operative on the fluid for at least one of reaction therewith and separation of components thereof.

13. The cuvette of claim 5 wherein the fluid-reception member is at least partly uncovered by at least one of the planar-shaped parts, whereby to provide access thereto for receiving the fluid.

14. The cuvette of claim 6 wherein the fluid-reception member is at least partly uncovered by at least one of the planar-shaped parts, whereby to provide access thereto for receiving the fluid.

15. The cuvette of claim 7 wherein the fluid-reception member is at least partly uncovered by at least one of the planar-shaped parts, whereby to provide access thereto for receiving the fluid.

16. The cuvette of claim 8 wherein the fluid-reception member is at least partly uncovered by at least one of the planar-shaped parts, whereby to provide access thereto for receiving the fluid.

17. The cuvette of claim 1, wherein one of the planar-shaped parts extends beyond the other for providing a handle to the cuvette.

18. The cuvette of claim 2, wherein one of the planar-shaped parts extends beyond the other for providing a handle to the cuvette.

19. The cuvette of claim 5, wherein one of the planar-shaped parts extends beyond the other for providing a handle to the cuvette.

20. The cuvette of claim 16, wherein one of the planar-shaped parts extends beyond the other for providing a handle to the cuvette.

* * * * *